(12) United States Patent
Mukai et al.

(10) Patent No.: US 9,107,779 B2
(45) Date of Patent: Aug. 18, 2015

(54) BODILY FLUID ABSORBENT ARTICLE INCLUDING BODILY FLUID ABSORBENT CORE AND METHOD FOR MAKING THE CORE

(75) Inventors: Hirotomo Mukai, Kanagawa (JP); Takaya Arayama, Kanagawa (JP)

(73) Assignee: UNICHARM CORPORATION, Ehime (JP)

( * ) Notice: Subject to any disclaimer, the term of this patent is extended or adjusted under 35 U.S.C. 154(b) by 70 days.

(21) Appl. No.: 13/878,649

(22) PCT Filed: Dec. 28, 2011

(86) PCT No.: PCT/JP2011/007366
§ 371 (c)(1),
(2), (4) Date: Apr. 10, 2013

(87) PCT Pub. No.: WO2012/090508
PCT Pub. Date: Jul. 5, 2012

(65) Prior Publication Data
US 2013/0289509 A1    Oct. 31, 2013

(30) Foreign Application Priority Data

Dec. 28, 2010 (JP) ................................. 2010-294192

(51) Int. Cl.
*A61F 13/15* (2006.01)
*A61F 13/535* (2006.01)
(Continued)

(52) U.S. Cl.
CPC ......... *A61F 13/535* (2013.01); *A61F 13/15658* (2013.01); *A61F 13/15699* (2013.01); *A61F 13/4756* (2013.01); *A61F 13/49466* (2013.01); *A61F 13/51* (2013.01);
(Continued)

(58) Field of Classification Search
CPC ................. A61F 13/51; A61F 13/511; A61F 13/511004; A61F 13/51108; A61F 13/5121; A61F 13/15
USPC ........... 604/378, 379, 380, 385.101, 375, 368
See application file for complete search history.

(56) References Cited

U.S. PATENT DOCUMENTS

| 5,846,231 A | 12/1998 | Fujioka et al. |
| 7,795,492 B2 * | 9/2010 | Vartiainen ..................... 604/378 |
| 2002/0065498 A1 | 5/2002 | Ohashi et al. |

FOREIGN PATENT DOCUMENTS

| EP | 0933074 A1 | 8/1999 |
| EP | 1210925 A2 | 6/2002 |

(Continued)

OTHER PUBLICATIONS

International Search Report issued in PCT/JP2011/007366 on Apr. 3, 2012.

*Primary Examiner* — Jacqueline Stephens
(74) *Attorney, Agent, or Firm* — Lowe Hauptman & Ham, LLP

(57) ABSTRACT

Provided are a bodily fluid absorbent article improved to absorb bodily fluids quickly and a method for making a core for the bodily fluid absorbent article. A bodily fluid absorbent core for a bodily fluid absorbent article is formed with one or more elongated depressions. The core 40 includes one or more surface layers and one or more inner sections lying inside the one or more surface layers. The one or more surface layers are formed primarily of liquid-absorbent fibers and the one or more inner sections are formed of the liquid-absorbent fibers and superabsorbent polymer particles.

7 Claims, 15 Drawing Sheets

(51) Int. Cl.
*A61F 13/475* (2006.01)
*A61F 13/494* (2006.01)
*A61F 13/51* (2006.01)
*A61F 13/511* (2006.01)
*A61F 13/53* (2006.01)
*A61F 13/537* (2006.01)

(52) U.S. Cl.
CPC .... *A61F 13/51104* (2013.01); *A61F 13/51108* (2013.01); *A61F2013/53051* (2013.01); *A61F 2013/53778* (2013.01); *A61F 2013/53782* (2013.01)

(56) References Cited

FOREIGN PATENT DOCUMENTS

| | | |
|---|---|---|
| EP | 2308432 A1 | 4/2011 |
| JP | 11216161 A | 8/1999 |
| JP | 2000234255 A | 8/2000 |
| JP | 3208289 B2 | 9/2001 |
| JP | 2002165834 A | 6/2002 |
| JP | 2006115996 A | 5/2006 |
| JP | 2007117727 A | 5/2007 |
| JP | 2007144104 A | 6/2007 |
| JP | 2007260297 A | 10/2007 |
| JP | 2010035588 A | 2/2010 |

* cited by examiner

BODILY FLUID ABSORBENT ARTICLE INCLUDING BODILY FLUID ABSORBENT CORE AND METHOD FOR MAKING THE CORE

RELATED APPLICATIONS

The present application is a National Phase of PCT/JP2011/007366, filed Dec. 28, 2011, and is based on, and claims priority from, Japanese Application No. 2010-294192, filed Dec. 28, 2010.

TECHNICAL FIELD

The present disclosure relates to bodily fluid absorbent articles each including a bodily fluid absorbent core and to methods for making the core and, more particularly, to bodily fluid absorbent articles suitable to be used as diapers, toilet-training pants, in-continent briefs or menstruation pads and bodily fluid absorbent cores for such bodily fluid absorbent articles.

BACKGROUND

Diapers each having a bodily fluid absorbent core containing fluid absorbent fibers and superabsorbent polymer particles are known. For example, JP 3208289 B (PTL 1) discloses a diaper having a longitudinal direction, a transverse direction and a thickness direction and including a core sandwiched between a liquid-pervious sheet and a liquid-impervious sheet. The core in this diaper is formed with slits extending therethrough in the thickness direction from a surface thereof facing the wearer's skin to a surface thereof facing away from the wearer's skin. These slits extend in the longitudinal direction.

In this diaper, bodily fluids such as urine flow along the slits and consequently the dispersion of bodily fluids in the longitudinal direction is accelerated.

CITATION LIST

Patent Literature

{PTL 1} JP 3208289 B

SUMMARY

Technical Problem

In a diaper disclosed in PTL 1, peripheral walls of the respective slits through the core contain a large quantity of superabsorbent polymer particles which are apt to form gel blocks upon absorption of bodily fluids. Such gel blocks may choke the slits and eventually may destroy the desired function of the slits or prevent bodily fluids from being quickly absorbed through the peripheral walls of the respective slits.

Solution to Problem

In a first aspect of the present invention, provided is a bodily fluid absorbent article including a bodily fluid absorbent core.

More specifically, in the article according to the first aspect of the invention, the core has a predetermined thickness and contains therein liquid-absorbent fibers and superabsorbent polymer particles and is covered with a liquid-pervious sheet on an upper surface thereof.

In this bodily fluid absorbent article, the core has a skin-facing surface and a non-skin-facing surface opposite to the skin-facing surface; at least one of the skin-facing surface and the non-skin-facing surface is formed with one or more elongated depressions sinking from the skin-facing surface toward the non-skin-facing surface; and the core includes one or more surface layers each formed of the liquid-absorbent fibers to define a peripheral wall or peripheral walls of the one or more elongated depressions and further includes an inner section lying inside the one or more surface layers and formed of the liquid-absorbent fibers and the superabsorbent polymer particles mixed together.

In a second aspect of the invention, provided is a method for making the bodily fluid absorbent core.

In the method for making the core, a process for making the core includes a step of feeding liquid-absorbent fibers to respective molds each having a concave area corresponding to a three-dimensional shape of the core wherein the concave area is defined by a bottom and a peripheral wall rising from the bottom; the respective peripheral walls of the molds are at least partially formed with a plurality of through-holes via which the one or more concave areas is capable of being subjected to a suction effect; and in the fiber feeding step, respective surfaces of the peripheral walls are at least partially covered with the liquid-absorbent fibers under the suction effect provided via the through-holes.

Advantageous Effects of Invention

In the bodily fluid absorbent article according to this invention, the surface layers defining the peripheral walls of the one or more elongated depressions of the bodily fluid absorbent core for the article are primarily formed of the liquid-absorbent fibers. With such unique feature, it is possible for these surface layers to prevent the superabsorbent polymer particles contained in the inner sections from moving in the core and from intruding into the elongated depressions where the superabsorbent polymer particles may absorb bodily fluids and form a gel block inside the one or more elongated depressions. In this way, it is possible for this bodily fluid absorbent core to absorb bodily fluids through the peripheral walls of the one or more elongated depressions.

DESCRIPTION OF EMBODIMENTS

Details of a bodily fluid absorbent article according to embodiments of the present invention will be more fully understood from the description of a pant-type disposable diaper as one of typical examples with reference to the accompanying drawings.

Figure 1:
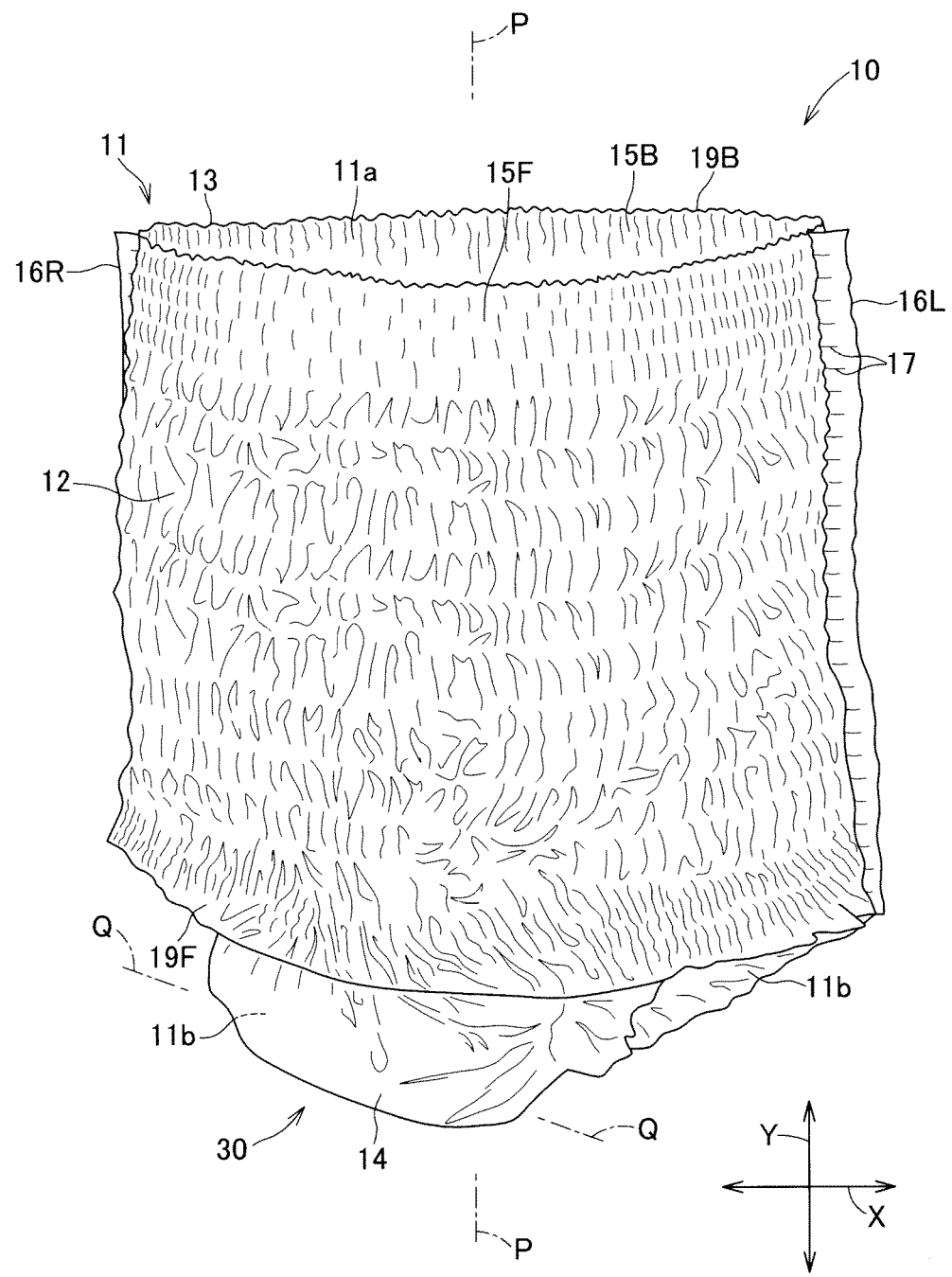
FIG. 1 is a perspective view of a disposable diaper as one example of a bodily fluid absorbent article in accordance with some embodiments of the present invention.

In the drawings, X and Y indicate a transverse direction and a longitudinal direction being orthogonal one to another with respect to the diaper 1 of FIG. 1. Line P-P is longitudinal center line bisecting a width dimension of a diaper 10 in the transverse direction X and line Q-Q is a transverse center line bisecting a width dimension of the diaper 10 in the longitudinal direction Y.

Referring to FIG. 1, the diaper 10 is provided with a chassis 11 including a front waist region 12, a rear waist region 13 and a crotch region 14 extending between the front waist region 12 and the rear waist region 13 in the longitudinal direction Y so that the chassis 11 may be shaped symmetrically about the longitudinal center line P-P.

The chassis 11 is contoured by front and rear ends 15F, 15R extending in the transverse direction X in the front and rear waist regions 12, 13, respectively, and opposite side edges 16R, 16L defined. The front and rear waist regions 12, 13 are coupled by the intermediary of the crotch region 14. The chassis 11 further includes a waist-opening 11a defined by the front and rear waist regions 12, 13 and a pair of leg-openings 11b defined by the front 12, the rear waist region 13 and the crotch region 14. Along the opposite side edges 16R, 16L, a plurality of seams 17 are arranged intermittently in the longitudinal direction Y.

Figure 2:
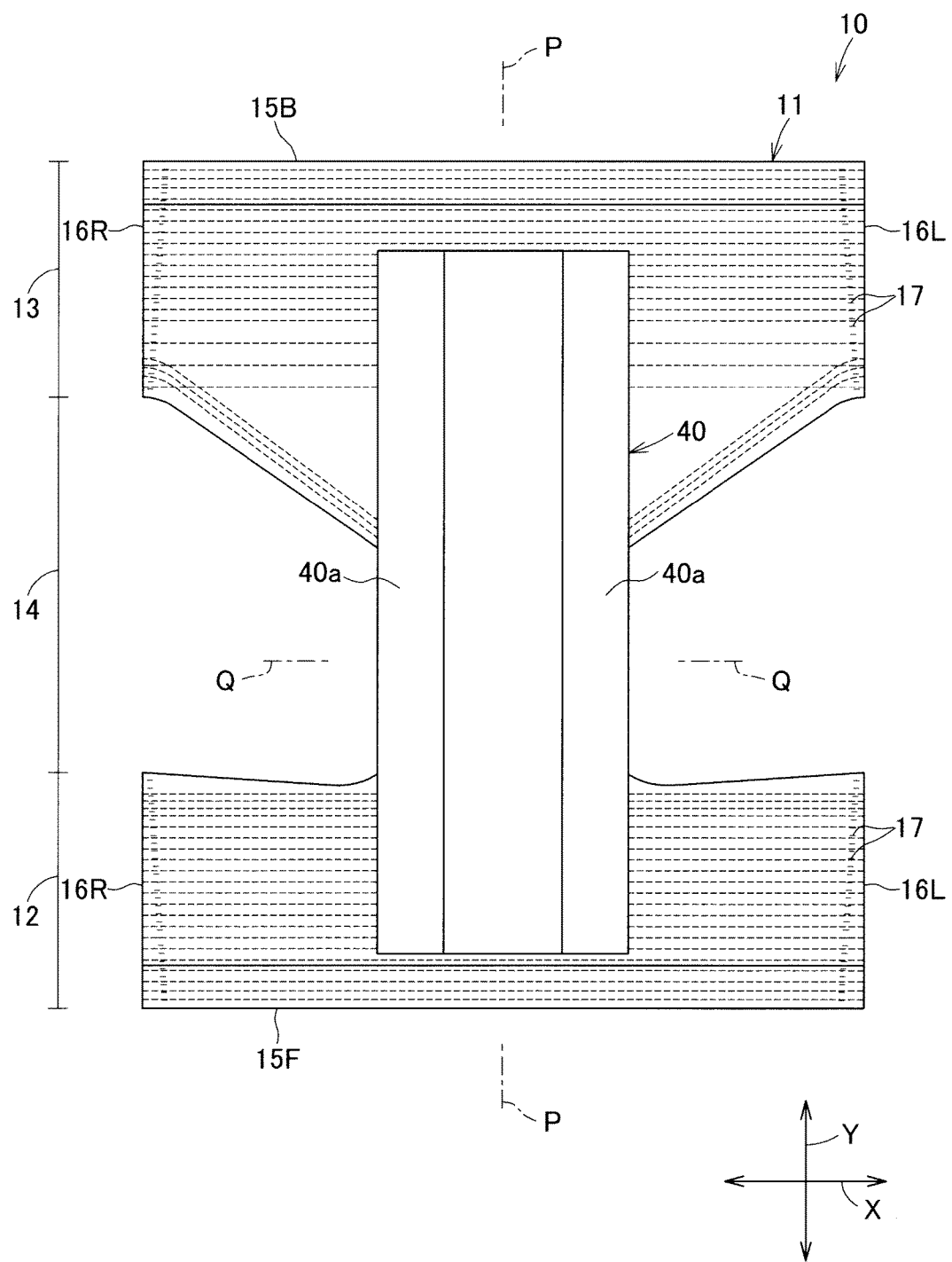
FIG. 2 is a partially cutaway plan view of the diaper of FIG. 1 flatly developed from the state shown in FIG. 1.

In FIG. 2, the developed diaper 10 is in the state where the front and rear waist regions 12, 13 of the diaper 10 of FIG. 1 are peeled off from each other at the seams 17 and then the diaper 10 is developed in the transverse direction X as well as in the longitudinal direction Y. The developed diaper 10 is shown as viewed from an inner surface side thereof. The inner surface side of the diaper 10 means a surface thereof facing the wearer's skin when the diaper 10 is put on the wearer's body and will be designated hereunder as a skin-facing surface.

Referring to FIG. 2, the diaper 10 includes the chassis 11 and a bodily fluid absorbent panel 40 attached to the inner surface of the chassis 11. The chassis 11 has a concave shape curved inwardly of the crotch region 14. The bodily fluid absorbent panel 40 extends across the crotch region 14 into the front waist region 12 and the rear waist region 13 and is provided along lateral sides thereof opposite in the transverse direction X with gasket cuffs 40a. The panel 40 functions to absorb and contain bodily fluids in its region defined between the gasket cuffs 40a.

Figure 3:
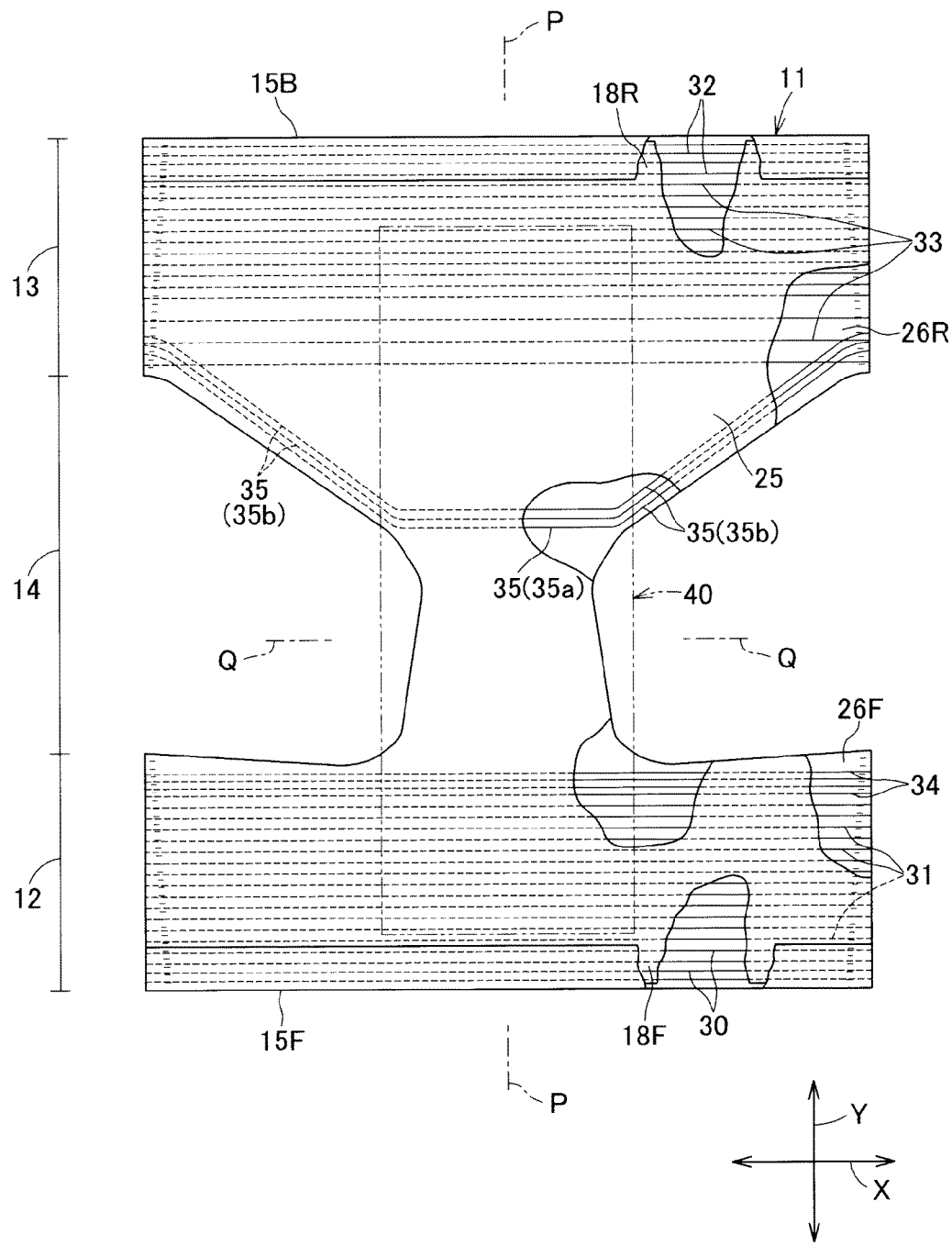
FIG. 3 is a partially cutaway plan view of a chassis of the diaper of FIG. 1.

In FIG. 3, the panel 40 is indicated by an imaginary line. The chassis 11 has a concave shape curved inwardly and includes an inner sheet 25 defining a part of the skin-facing surface of the diaper 10, a front outer sheet 26F bonded from the outside of the diaper 10 to the inner sheet 25 in the front waist region 12 with hot melt adhesives (not shown) and a rear outer sheet 26R bonded from the outside of the diaper 10 to the inner sheet 25 in the rear waist region 13 with hot melt adhesives (not shown). The front outer sheet 26F and the rear outer sheet 26R are folded along the front and rear ends 15F, 15B of the diaper 10, respectively, so as to cover opposite ends 18F, 18R of the inner sheet 25 as viewed in the longitudinal direction Y in FIG. 3 from the inside of the diaper 10.

The front waist region 12 of the chassis 11 includes a plurality of front first waist elastic members 30, a plurality of front second waist elastic members 31 and a plurality of front leg elastic members 34. The front first waist elastic members 30 and the front second waist elastic members 31 extend in the transverse direction X between the opposite side edges of the front waist region 12 and are disposed between the inner sheet 25 and the front outer sheet 26F and secured under tension to at least one of these sheets 25, 26F with hot melt adhesives (not shown).

The rear waist region 13 of the chassis 11 includes a plurality of rear first waist elastic members 32 and a plurality of rear second waist elastic members 33. The rear first waist elastic members 32 and the rear second waist elastic members 33 extend in a transverse direction X between the opposite side edges of the rear waist region 13 and are disposed between the inner sheet 25 and the rear outer sheet 26R and secured under tension to at least one of these sheets 25, 26R with hot melt adhesives (not shown).

Rear leg elastic members 35 are located in the crotch region 14 and disposed between the inner sheet 25 and the rear outer sheet 26R. Opposite lateral segments 35b of these rear leg elastic members 35 respectively extend along portions defining peripheral edges of the respective leg-openings 11b (See FIG. 1) to intersect diagonally with the longitudinal center line P-P. Middle segments 35a of the rear leg elastic members 35 extend across the crotch region 14 orthogonally to the longitudinal center line P-P. These rear leg elastic members 35 also are secured under tension to at least one of the inner sheet 25 and the rear outer sheet 26R with hot melt adhesives (not shown).

In such chassis 11, the inner sheet 25 may be formed of one or more sheet materials selected from the group including nonwoven fabrics of thermoplastic synthetic fibers, plastic films, nonwoven fabric-plastic film laminates. Preferably, liquid-impervious sheets are used and, more preferably, air-permeable and liquid-impervious sheets are used as the sheet materials. One of typical examples of the inner sheet 25 is an SMS (spun bonded/melt blown/spun bonded) nonwoven fabric of polypropylene fibers.

The front outer sheet 26F and the rear outer sheet 26R are preferably formed of nonwoven fabrics of thermoplastic synthetic fibers such as spun bonded nonwoven fabrics, point bonded nonwoven fabrics or SMS nonwoven fabrics so that the outer surface of the chassis 11 may provide a cloth-like feeling to the wearer's skin. One of typical examples of the front outer sheet 26F and the rear outer sheet 26R is a spun bonded nonwoven fabric of polypropylene having a basis mass (i.e., mass per unit area) of about 17 g/m$^2$.

As the front first and second waist elastic members 30, 31, the front leg elastic members 34, the rear first and second waist elastic members 32, 33 and the rear leg elastic members 35, in addition to shreds or strings of synthetic rubber such as Spandex™ or natural rubber, sheet strips of elastically stretchable nonwoven fabric or urethane rubber may be used. Assuming that the diaper 10 of FIG. 1 is an adult diaper and Spandex™ is used as the elastic members, 4 to 8 elastic members each having a fineness ranging from about 700 to about 1200 dtex may be used under tension at a tensile ratio ranging from about 2.0 to about 4.0 as the front first waist elastic members 30 and the rear first waist elastic members 33, respectively, and 7 to 20 elastic members each having a fineness ranging from about 400 to about 1200 dtex may be used under tension at a tensile ratio ranging from about 1.4 to about 4.0. On the same assumption, 2 to 6 elastic members each having a fineness ranging from about 400 to about 1000 dtex may be used under tension at a tensile ratio ranging from 0 to about 3.5 as the front leg elastic members 34 and 2 to 6 elastic members each having a fineness ranging from about 400 to about 1000 dtex may be used under tension at a tensile ratio ranging from 0 to about 1.8 as the middle segments 35a extending across the crotch region 14 and 2 to 6 elastic members under tension at a tensile ratio ranging from about 2.0 to about 2.5 as the lateral segments 35b extending to intersect diagonally with the longitudinal center line P-P, respectively. The tensile ratio of the middle segments 35a of the rear leg elastic members 35 orthogonally intersecting with the longitudinal center line P-P may be set to be lower than the tensile ratio of the respective lateral segments 35b to prevent a shape of respective elongated depressions 43R, 43L, formed in the absorbent panel 40 in the vicinity of the longitudinal center line P-P as will be described later, from being affected by the middle segments 35a. The tensile ratio of the lateral segments 35b may be set to be relatively high to assure that the absorbent panel 40 is pulled in the longitudinal direction Y in the vicinities of the opposite edges 16R, 16L (See FIG. 4) thereof and thereby the absorbent panel 40 is prevented from being displaced in the transverse direction X when the diaper 10 is put on the wearer's body.

Figure 4:
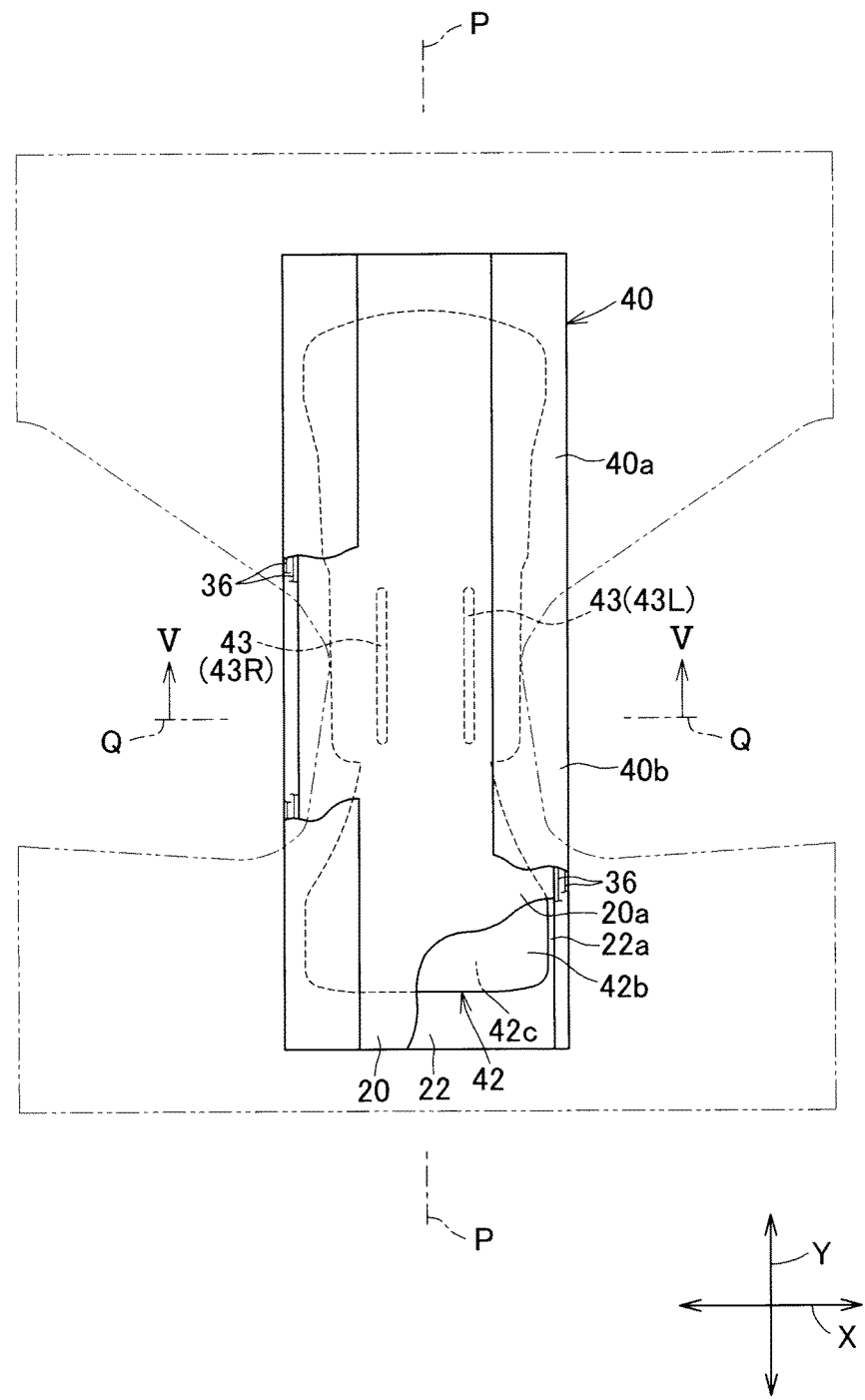
FIG. 4 is a partially cutaway plan view of a bodily fluid absorbent panel of the diaper of FIG. 1.

In FIG. 4, the chassis 1 is indicated by imaginary line. The panel 40 includes a liquid-pervious bodyside liner 20, a liquid-impervious backsheet 22 and the bodily fluid absorbent core 42 disposed between these two elements 20, 22 and, in addition, the gasket cuffs 40a extending in the longitudinal direction Y along both lateral sides of the panel 40 opposite to each other in the transverse direction X.

The bodyside liner 20 may be formed, for example, of fibrous nonwoven fabrics, laminates of two or more fibrous nonwoven fabric layers or perforated plastic films. When the bodyside liner 20 is formed of a fibrous nonwoven fabric, the fibrous nonwoven fabric may be, for example, air-through nonwoven fabrics, spun bonded nonwoven fabrics or point bonded nonwoven fabrics each having a mass per unit area (i.e., basis mass) ranging from about 15 to about 50 g/m$^2$, more preferably ranging from about 20 to about 35 g/m$^2$. The bodyside liner 20 exemplarily shown is formed of a point bonded nonwoven fabric having a mass per unit area of 23 g/m$^2$ and, in this nonwoven fabric, polypropylene fibers have previously been treated to become hydrophilic.

The backsheet 22 may be formed of liquid-impervious plastic films and more preferably of liquid-impervious and moisture-pervious plastic films.

The gasket cuffs 40a may be formed of hydrophobic nonwoven fabrics or liquid-impervious plastic films and the exemplarily illustrated gasket cuffs 40a are formed of a SMS nonwoven fabric of propylene fibers having a mass per unit area of about 15 g/m$^2$. The gasket cuffs 40a are folded to form sleeves, respectively, a plurality of elastic members 36 are secured under tension within the respective sleeves with hot melt adhesives (not shown). As the elastic members 36, Spandex™ having a fineness ranging from about 400 to about 1000 dtex are secured under tension at a tensile ratio ranging from about 1.5 to about 3.

The core 42 includes liquid-absorbent fibers such as fluff wood pulp fibers and superabsorbent polymer particles. The core 42 is formed with elongated depressions 43 (43R, 43L) extending therethrough from its skin-facing surface 42b toward its non-skin-facing surface 42c (See FIGS. 5 and 6). The elongated depressions 43R, 43L are symmetric about the longitudinal center line P-P and extend in the longitudinal direction Y.

Figure 5:
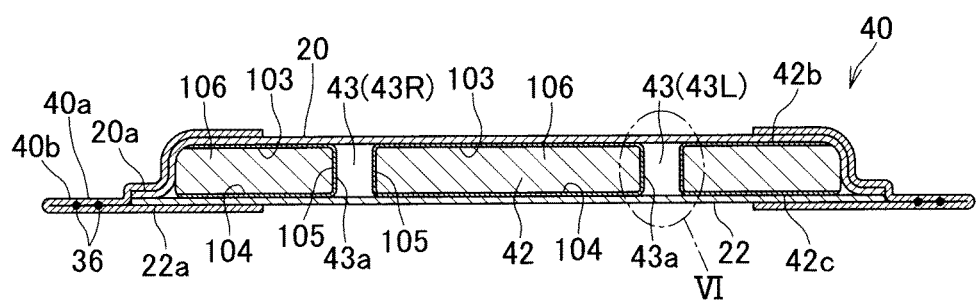
FIG. 5 is a sectional view of the diaper taken along line V-V in FIG. 4.

In FIG. 5, line V-V corresponds to a transverse center line Q-Q bisecting a dimension of the diaper 10 in the longitudinal direction Y.

In the panel 40 of FIG. 5, the core 42 has a skin-facing surface 42b and the non-skin-facing surface 42c wherein, of the skin-facing surface 42b and the non-skin-facing surface 42c, at least the surface 42b for facing the wearer's skin is covered with the bodyside liner 20 and, in the exemplarily shown embodiment, the non-skin-facing surface 42c is covered with the backsheet 22. These two elements 20, 22 are attached to the core 42 with hot melt adhesives (not shown). It should be appreciated that the skin-facing surface is sometimes designated as a top surface 42b of the core 42 and the non-skin-facing surface is sometimes designated as a bottom surface 42c of the core 42 in this specification. While the top surface 42b of the core 42 is formed with a pair of the elongated depressions 43 (43L, 43R), these elongated depressions 43 are provided in the form of through-holes sinking from the top surface 42b to the bottom surface 42c, having peripheral walls 43a and extending in the longitudinal direction Y as viewed in FIG. 4. These elongated depressions 43 may, however, be provided in the form of grooves each having a relatively thin bottom. Respective side edges 20a, 22a of the bodyside liner 20 and backsheet 22 extend outward beyond the side edges of the core 42 and are bonded together with hot melt adhesives (not shown). The gasket cuffs 40a are bonded to the side edges 20a of the bodyside liner 20 and the side edges 22a of the backsheet 22 with hot melt adhesives (not shown) and include within the sleeve-like side edges 40b two elastic members 36 secured under tension to the inner surfaces of the respective sleeve-like side edges 40b.

Figure 6:
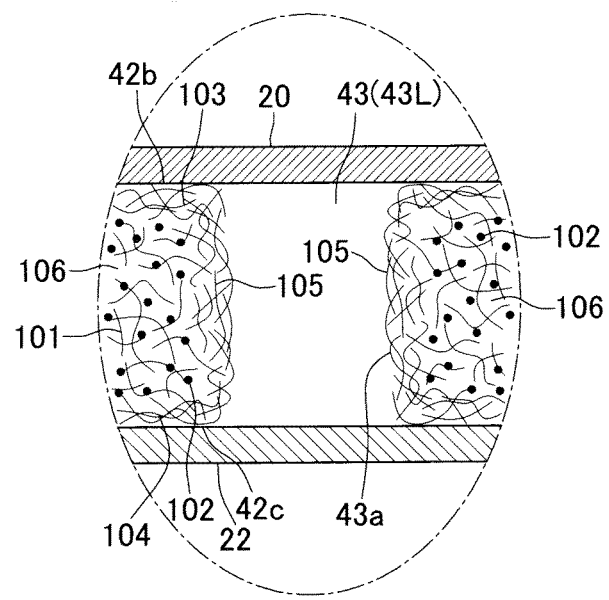
FIG. 6 is a scale-enlarged diagram of a circled region in FIG. 5.

Referring to FIG. 6, the core 42 contains fluff wood pulp fibers as liquid-absorbent fibers 101 and the superabsorbent polymer particles 102. It should be appreciated that the liquid-absorbent fibers will be sometimes designated as fluff wood pulp fibers 101 hereinafter. In the core 42, the top surface 42b, the bottom surface 42c and the peripheral walls 43a are respectively defined by surface layers 103, 104, 105 which are formed, in turn, entirely or substantially entirely of the fluff wood pulp fibers 101. In other words, the surface layers 103, 104, 105 are free or substantially free of superabsorbent polymer particles. In respective medial regions (inner sections) 106 surrounded (or covered) by the surface layers 103, 104, 105, the fluff wood pulp fibers 101 and the superabsorbent polymer particles 102 are mixed together at an almost constant ratio. While the surface layers 103, 104, 105 also may contain the superabsorbent polymer particles 102, the surface layers 103, 104, 105 are distinguished from the medial regions 106 in that the superabsorbent polymer particles 102 which may be present therein is at a much lower ratio to the liquid-absorbent fibers than in the medial regions 106. In other words, the content of the superabsorbent polymer particles 102 remarkably increases from the surface layers 103, 104, 105 toward the medial regions 106. In FIG. 5, the medial regions 106 are shown to distinguish the medial regions 106 schematically from the surface layers 103, 104, 105.

The content of the superabsorbent polymer particles 102 in the surface layers 103, 104, 105 and the medial regions 106 was visually compared using colored physiological saline obtained by dissolving edible colorant "Blue No. 1"—Brilliant Blue FCF ("Yacht-mark edible colorant" available from KOYO PRODUCK Co., Ltd.) of 1% by mass in 0.9% physiological saline. Five test pieces of the core 42 were prepared for observation and 30, 60, 90, 120 and 150 ml of colored physiological saline were dropped onto the respective test pieces 42 from directly above the concave regions at a rate of 10 ml/sec and 3 minutes after dropping of colored physiological saline, coloration states in the vicinities of the elongated depressions 43 in the respective test pieces 42 were observed. The one of these 5 test pieces 42 for which the colored physiological saline dropped thereon has been apparently excessive beyond its absorption capacity was set aside and observation was conducted on the other four test pieces 42. In the test piece 42, the region containing a large quantity of superabsorbent polymer particles 102 is colored in correspondingly darker blue and the region containing a large quantity of fluff wood pulp fibers is colored in correspondingly lighter blue. In this way, it is possible to know whether the content of superabsorbent polymer particles is rich or poor. When it is difficult to determine whether the blue color in the medial regions merely by observation from the outside of the test piece 42, the test piece 42 may be held by both hands and cleaved in to along imaginary line extending across the elongated depression 43 and the cross-section of the test piece 42 may be observed. For operating of dropping the colored physiological saline, preferably a burette having a capacity of at least 150 ml is used.

Figure 7:
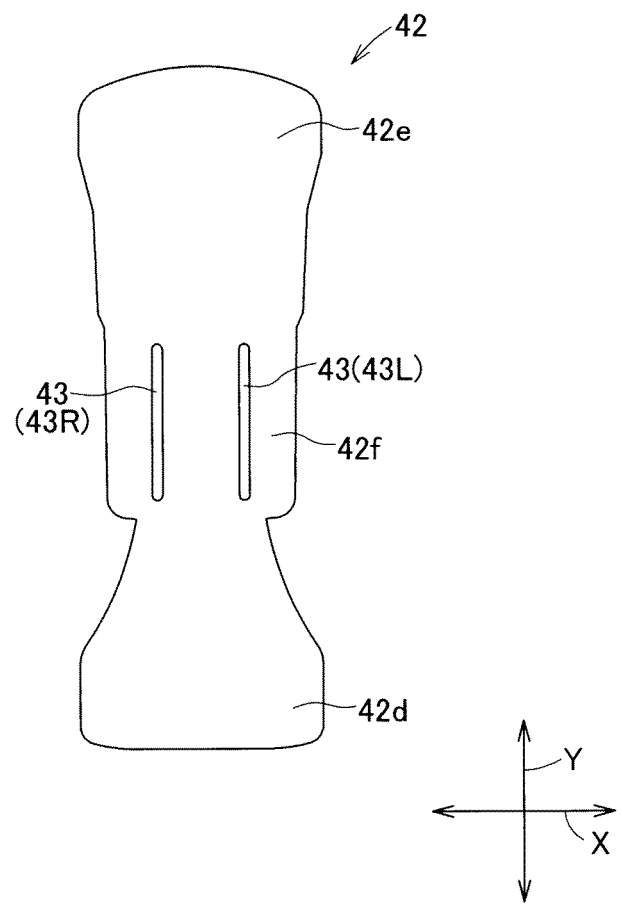
FIG. 7 is a plan view showing the core in FIG. 4.

In FIG. 7, the fluff wood pulp fibers 101 as well as the superabsorbent polymer particles 102 are not shown. The core 42 is contoured so that its width dimension is relatively larger in a front section 42d lying in the front waist region 12 as well as in a rear section 42e lying in the rear waist region 13 and slightly smaller in a middle section 42f lying in the crotch region 14 wherein the middle section 42f is formed with a pair of the elongated depressions 43 (43R, 43L).

In the panel 40 of FIG. 2 including the core 42 formed as has been described above, bodily fluids such as urine having passed through the bodyside liner 20 and then flow into the elongated depressions 43. Now bodily fluids are dispersed as bodily fluids move along the respective elongated depressions 43, for example, in the longitudinal direction Y and are absorbed by the core 42 through the surface layers 105. Compared to the core not formed with the elongated depressions 43, absorption of bodily fluids by the core 42 is further improved since a contact area between bodily fluids and the core 42 is effectively enlarged by the respective peripheral walls of the elongated depressions 43. In addition, along the peripheral walls 43a, bodily fluids can be easily dispersed in the longitudinal direction Y and/or the thickness direction in the surface layers 105 primarily formed of the fluff pulp wood fibers 101 under the effect of capillary phenomenon. In the surface layers 103, 104, bodily fluids are easily dispersed in the transverse direction X as well as in the longitudinal direction Y. In the panel 40, the core 42 can be utilized over its entire area for absorption of bodily fluids.

The surface layers 105 of the peripheral walls 43a function also to help prevent the superabsorbent polymer particles 102 from intruding from the medial regions 106 into the elongated depressions 43 even when the core 42 of the diaper 10 put on the wearer's body is deformed due to movements of the wearer's body and the superabsorbent polymer particles 102 contained in the medial regions 106 move. Consequently, there is a low likelihood that the superabsorbent polymer particles 102 might intrude into the elongated depressions 43, at least partially clog up the elongated depressions 43 and disturb a smooth flow of bodily fluids along the elongated depression 43.

The function of the surface layers 103, 104, 105 to help dispersion of bodily fluids in this manner permits the core 42 containing the superabsorbent polymer particles 102 to be formed with a thickness as thin as ranging from about 1 to about 5 mm. The superabsorbent polymer particles 102 have no particularly advantageous property for dispersion of bodily fluids and the presence of the superabsorbent polymer particles 102 is rather undesirable when it is desired to disperse bodily fluids quickly over the entire area of the core 42 so that bodily fluids may be absorbed by the core 42 as quickly as possible. However, the core 42 includes the surface layers 103, 104, 105 as seen in the exemplarily illustrated embodiment and these surface layers make it possible for the core 42 to absorb bodily fluids quickly. It should be noted here that the present invention is not limited to the exemplarily illustrated embodiment. Specifically, it is possible without departing from the scope of the invention to use the core 42 formed with the surface layers 105 but without any one or both of the surface layers 103, 104. The thickness of the respective surface layers 105 is preferably ranging from about 0.2 to about 3 mm and, more preferably ranging from about 0.4 to about 2 mm. While one of the preferred liquid-absorbent fibers is fluff wood pulp fibers, the fluff wood pulp fibers may be replaced by the other liquid-absorbent fibers such as staples of rayon fibers or such fibers mixed with the fluff wood pulp fibers. The exemplarily illustrated core 42 may be replaced by the core wrapped with an appropriate wrapping sheet such as a tissue paper. The elongated depressions 43 of the core 42 provided in the form of elongated depressions may be replaced by bottomed elongated depressions each having a depth extending from the skin-facing surface 42b of the core 4 toward the non-skin-facing surface 42c of the core 4, or vice versa.

The exemplarily illustrated core 42 according to the invention may be used as the bodily fluid absorbent core in various bodily fluid absorbent articles, such as incontinent briefs and menstruation pads by making appropriate changes to its planar shape or cross-sectional shape and/or the other factors such as the shape, the number and the location of the grooves.

Figure 8:
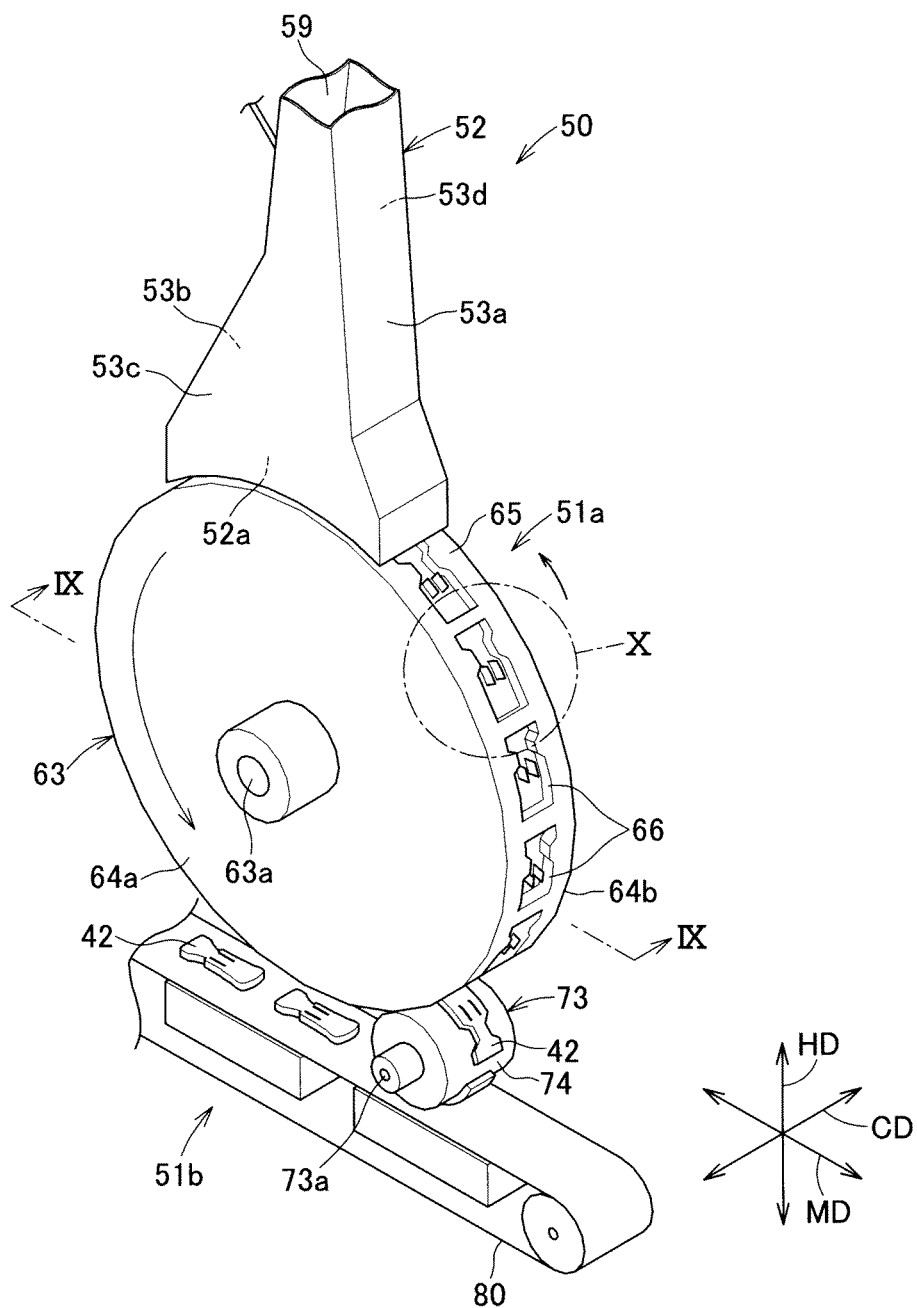
FIG. 8 is a partial perspective view illustrating a part of a process for making the core of the diaper of FIG. 1.
Figure 9:
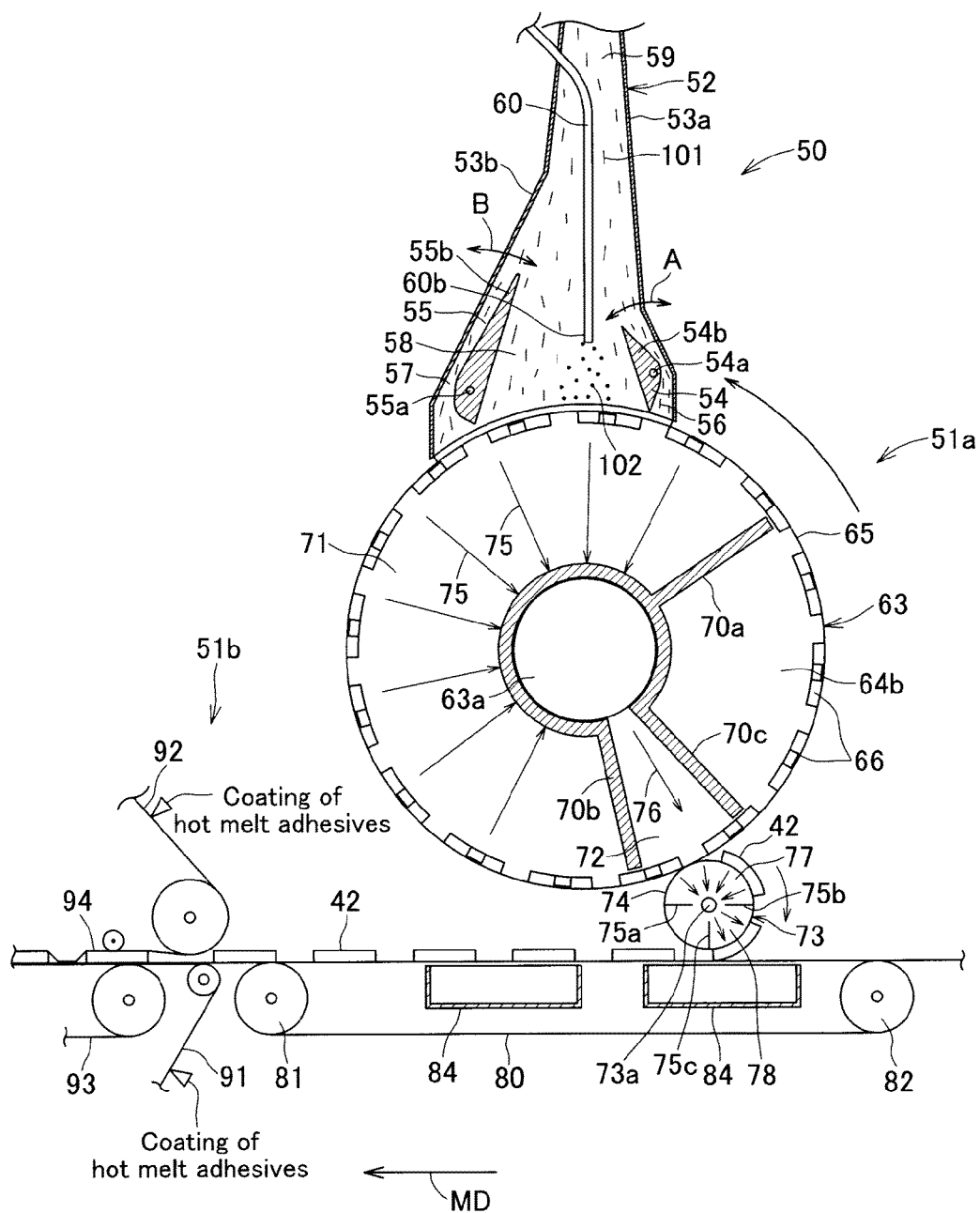
FIG. 9 is a part of the process for making the core.

A process for making such core 42 will be now exemplarily described with reference to the accompanying drawings. In FIGS. 8 and 9, MD designates a machine direction, CD designates a cross (intersection) direction which is orthogonal to the machine direction MD, and HD designates a height direction which is orthogonal to the directions MD, CD.

An apparatus 50 is provided with a molding section 51a adapted to mold the core 42 exemplarily shown in FIGS. 4 and 7 and a conveyor section 51b adapted to convey the molded core 42 by a first conveyor belt 80 in the machine direction MD. The molding section 51a includes a conduit 52, a first rotary drum 63 adapted to rotate about a rotary shaft 63a in a counterclockwise direction corresponding to the MD direction and a second rotary drum 73 adapted to rotate about the rotary shaft 73a.

The conduit 52 is located above the first rotary drum 63 and defined by a pair of peripheral walls 53a, 53b opposite to each other in the machine direction MD and a pair of peripheral walls 53c, 53d opposite to each other in the cross direction CD wherein a lower opening 52a of the conduit 52 faces a peripheral surface 65 of the first rotary drum 63. The lower opening 52a extends along the peripheral surface 65 of the first rotary drum 63 so that a predetermined clearance may be kept between the lower opening 52a and the peripheral surface 65. Of the peripheral walls of the conduit 52 defining the lower opening 52a, the paired peripheral walls 53a, 53b opposite to each other in the machine direction MD are spaced from each other along the peripheral surface 65 of the first rotary drum 63 by a dimension larger than a length dimension of a mold 66 described later.

Within the conduit 52, there are provided a first movable partition wall 54 lying on the upstream side as viewed in the machine direction MD and a second movable partition wall 55 lying on the downstream side as viewed in the machine direction MD. These first and second movable partition walls 54, 55 can be controlled so that respective distal ends 54b, 55b may swing about associated pivot shafts 54a, 55a extending in the cross direction CD in directions indicated by double-headed arrows A, B, respectively. With the swinging distal ends 54b, 55b spaced from the peripheral walls 53a, 53b, respectively, the first and second movable partition walls 54, 55 are postured to form the core 42 with the surface layers 103, 104, 105. In contrast, with the swinging distal ends 54b, 55b kept in contact with the peripheral walls 53a, 53b, the first and second movable partition walls 54, 55 are postured not to form the core 42 with the surface layers 103, 104, 105.

With the first and second movable partition walls 54, 55 postured to form the core 42 with the surface layers 103, 104, 105, first and second divergent pathways 56, 57 are defined between the first and second movable partition walls 54, 55 and the peripheral walls 53a, 53b of the conduit 52, respectively, and a central pathway 58 is defined between the first and second movable partition walls 54, 55. These pathways extend from the upstream side to the downstream side in the machine direction MD within the conduit 52. The first and second divergent pathways 56, 57 as well as the central pathway 58 are laterally closed by the peripheral walls 53c, 53d (See FIG. 8) which are opposite to each other in the cross direction CD.

The conduit 52 is additionally formed with a fiber feeding port 59 and a polymer particle feeding duct line 60. The fiber feeding port 59 is located at a top of the conduit 52 and functions to feed liquid-absorbent fibers 101 into the conduit 52.

The polymer particle feeding duct line 60 is used to feed the superabsorbent polymer particles 102 into the conduit 52 and includes an outlet 60b adapted to discharge the polymer particle feeding duct line 60 toward the first rotary drum 63. The outlet 60b is located below the fiber feeding port 59, between the first and second movable partition walls 54, 55 so as to be spaced from the peripheral surface 65 of the first rotary drum 63.

With the first and second movable partition walls 54, 55 postured to form the core 42 with the surface layers 103, 104, 105, the liquid-absorbent fibers 101 fed from the fiber feeding port 59 are dispersed into the first and second divergent pathways 56, 57 and the central pathway 58 in the course of falling onto the peripheral surface 65 of the first rotary drum 63. The superabsorbent polymer particles 102 are fed exclusively via the central pathway 58 and then mixed with the liquid-absorbent fibers preferably at a uniform mixing ratio before accumulation on the peripheral surface 65.

The first rotary drum 63 is provided in the form of a hollow circular cylinder defined by opposite side surfaces 64a, 64b and the peripheral surface 65. The peripheral surface 65 includes a plurality of the molds 66 each depressed inward in a radial direction of the first rotary drum 63. These molds 66 are arranged at predetermined pitches in a circumference direction of the first rotary drum 63.

Corresponding to the three-dimensional shape of the core 42, the mold 66 includes concave area 67a and a pair of ridges 67b defined by bottom 68 and walls 69a, 69b rising up from the bottom 68. The wall 69a defines the peripheral wall of the concave area 67a and the wall 69b defines the peripheral wall of the ridge 67b. These walls 69a, 69b may be tapered at an appropriate angle so that the core 42 can be easily released from the mold 66. Of the walls 69a, 69b, at least the wall 69b and the bottom 68 are respectively formed with a plurality of through-holes 69c and a plurality of through-holes 68c so that interior and exterior of the first rotary drum 63 may communicate with each other via these through-holes 69c and 68c. In this embodiment of the invention, it is also possible to form the wall 69a also with through-holes each having an appropriate inner diameter and arranged at appropriately regular pitches.

Figure 10:
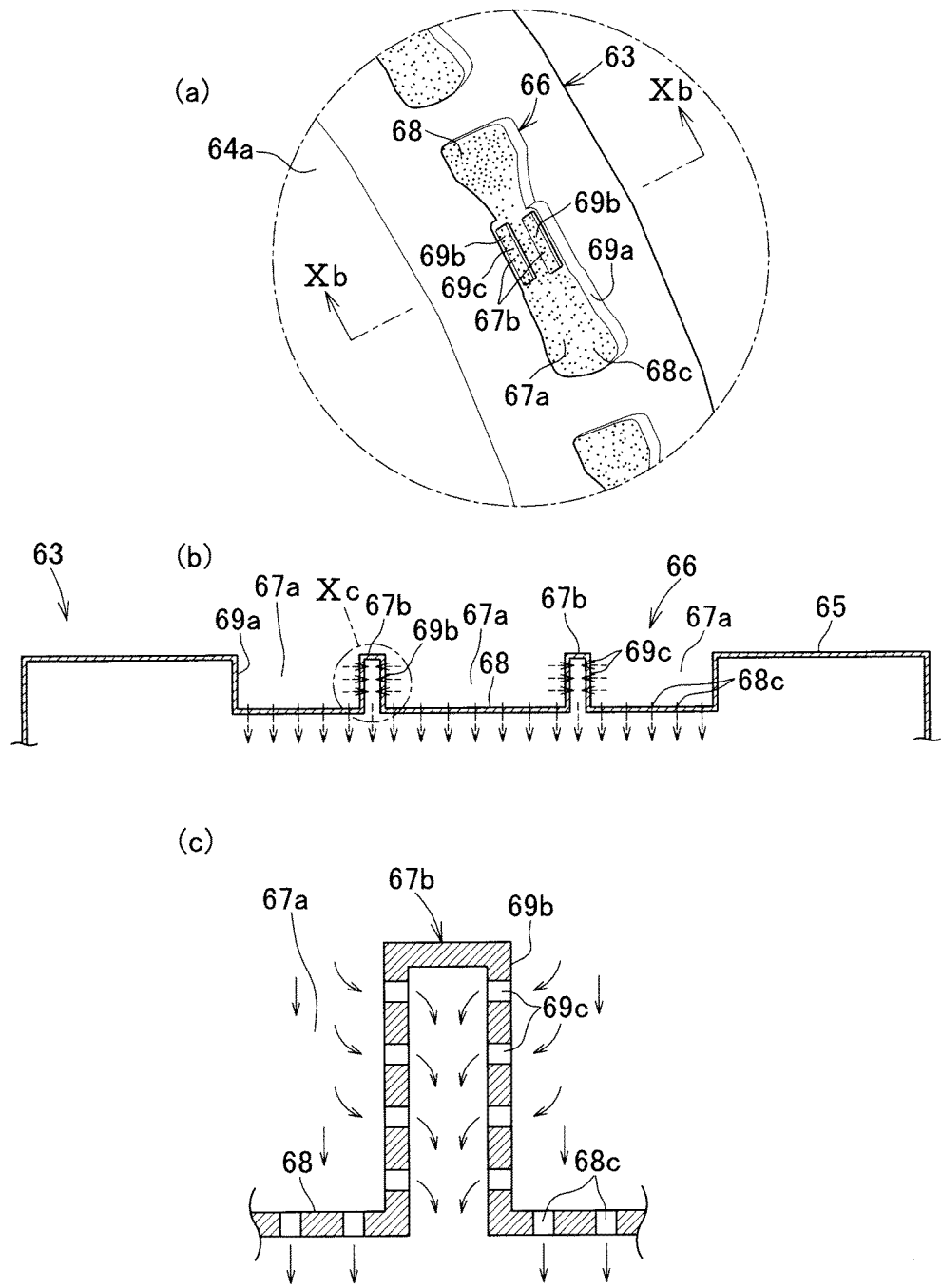
FIG. 10($a$) is a partial perspective view of a first rotary drum, FIG. 10($b$) is a sectional view taken along line Xb-Xb in FIG. 10($a$), and FIG. 10($c$) is a scale-enlarged view of a circled region Xc in FIG. 10($b$).

Referring again to FIGS. 8 and 9, inside the first rotary drum 63, partition walls 70a, 70b, 70c extend in the radial direction from a peripheral surface of the rotary shaft 63a. In a first zone 71 defined by the partition walls 70a, 70b, the air present therein is evacuated out from the first rotary drum by a suction unit intercommunicating with the first zone 71 via the interior of the rotary shaft 63a. In a second zone 72 defined by the partition walls 70b, 70c, a stream of pressurized air 76 is supplied to the second zone 72 from an external air supply unit intercommunicating with the second zone 72 via the interior of the rotary shaft 63a. When the molds 66 formed on the peripheral surface 65 of the first rotary drum 63 are moving in the first zone 71 during rotation of the first rotary drum 63, the stream of air 75 present in the concave areas 66 of the respective molds 66 is sucked via the through-holes 68c, 69c (See FIGS. 10(a) and 10(b)) of the respective molds 66 and thereby a suction pressure is exerted to the respective concave areas 67a. When the molds 66 formed on the peripheral surface 65 of the first rotary drum 63 move into the second zone 72 during rotation of the first rotary drum 63, pressurized air 76 is ejected to the second zone 72 and therefrom toward the concave areas 67a of the molds 66 via the through-holes 68c, 69c.

The second rotary drum 73 has a cylindrical peripheral surface 74 formed with a plurality of air holes (not shown) intercommunicating with the interior of the second rotary drum 73. Within the second rotary drum 73, partition walls 75a, 75b, 75c extending from a peripheral surface of the rotary shaft 73a in a radial direction. A first zone 77 defined within the second rotary drum 73 by the partition walls 75a, 75b faces the second zone 72 of the first rotary drum 63 by the intermediary of the peripheral surface 74 so that the air present in the first zone 77 is sucked by an external suction unit (not shown) intercommunicating with the first zone 77 via the interior of the rotary shaft 73a. A second zone 78 of the second rotary drum 73 defined by the partition walls 75b, 75c faces the first conveyor belt 80 by the intermediary of the peripheral surface 74. In the second zone 78, pressurized air is ejected outward from the second rotary drum 73 by an external air supply unit (not shown) intercommunicating with the second zone 78 via the interior of the rotary shaft 73a. The first rotary drum 63 cooperates with the second rotary drum 73 so that when the core 42 molded by the molds 66 on the peripheral surface of the first rotary drum 63 faces the peripheral surface 74 of the second rotary drum 73 during rotation of the first rotary drum 63, a suction pressure is exerted on the core 42 through air holes extending through the peripheral surface 74 of the second rotary drum 73 and, in consequence, the core 42 is transferred from the peripheral surface 65 of the first rotary drum 63 to the peripheral surface 74 of the second rotary drum 73. When the peripheral surface 74 moves to the second zone 78 of the second rotary drum 73, a stream of pressurized air supplied via the second zone 78 is ejected via the air holes of the peripheral surface 74 toward the core 42 and consequently the core 42 is transferred from the peripheral surface 74 onto the first conveyor belt 80.

The first conveyor belt 80 is of air-through type and cooperates with a driving roller 81 and a driven roller 82 to move along an orbit defined by these driving- and driven rollers 81, 82. The first conveyor belt 80 is formed with a plurality of through-holes (not shown). Between the driving roller 81 and the driven roller 82, an appropriate number of suction boxes 84 adapted to suck the air present above the first conveyor belt 80. These suction boxes 84 may be actuated to immobilize the cores 42 on the first conveyor belt 80. The first conveyor belt 80 faces the second zone 78 of the second rotary drum by the intermediary of the peripheral surface 74 thereof.

On the downstream side of the first conveyor belt 80, a first web 91 corresponding to the continuous bodyside liner 20 and a second web 92 corresponding to the continuous backsheet 22 both coated with hot melt adhesives are supplied to dispose the cores 42 and thereby to form a composite web 94 forming the cores 42, the first web 91 and the second web 92. The composite web 94 is loaded on a second conveyor belt 93 and conveyed further in the machine direction MD. In the subsequent steps, a pair of webs each corresponding to the uncut continuous gasket cuff 40a are attached to the composite web 94 to form a composite web (not shown) corresponding to the uncut continuous panel 40 and finally the composite web 94 of the uncut continuous panel 40 is cut along a line defined between each pair of the adjacent cores 42 to obtain the individual panels 40. While the exemplarily illustrated process may include a step of press-working the panels 40, illustration of such press-working step is eliminated for convenience of illustration.

Operation of the apparatus 50 may be initiated by pivotally posturing the first movable partition wall and/or the second movable partition wall 55 so that at least the surface layer 104 and the surface layer 105 of the surface layers 103, 104, 105 can be formed.

Then the interior of the conduit 52 is fed with fluff wood pulp fibers 101 used as the liquid-absorbent fibers and superabsorbent polymer particles 102. Simultaneously, the first and second rotary drums 63, 69 are rotated and the first conveyor belt 80 is activated to travel.

In the upstream region in the conduit 52 as viewed in the machine direction MD, fluff wood pulp fibers 101 only are fed into the first divergent pathway 56. The fluff wood pulp fibers 101 having passed through the first divergent pathway 56 are fed to the molds 66 formed on the peripheral surface 65 in the first zone 71. Under the suction effect working via the through-holes 68c, 69c (See FIG. 10(c)) extending through the bottoms 68 and the walls 69b of the respective molds 66, the fluff wood pulp fibers 101 is accumulated on the surfaces of the respective bottoms 68 and walls 69b. When the molds 66 of which the walls 69a are formed with the through-holes 69c, the fluff wood pulp fibers are accumulated on the walls 69a also. As for a pair of the ridges 67b formed on each of the molds 66, various alternative embodiments may be contemplated. For example, the paired ridges 67b may be partially formed with the through-holes 69c or only one of the paired ridges 67b may be formed with the through-holes 69c.

When the molds 66 come just under the central pathway 58 as the first rotary drum 63 rotates, fluff wood pulp fibers 101 and superabsorbent polymer particles 102 are accumulated in a mixed state in the respective molds 66.

In the exemplarily illustrated process, the molds 66 may be supplied with superabsorbent polymer particles 102 after the predetermined fluff wood pulp fibers has been accumulated on the bottoms 68 and the walls 69b of the respective molds 66 to assure that the through-holes 68c and the through-holes 69c extending through the bottoms 68 and the walls 69b are air-permeably covered with appropriate fluff wood pulp fibers. In consequence, it is possible to avoid a problem that superabsorbent polymer particles 102 might intrude into the through-holes 68c and the through-holes 69c and eventually clog these through-holes 68c, 69c.

In FIGS. 11 through 14, a core in accordance with another embodiment of the present invention is illustrated.

Figure 11:
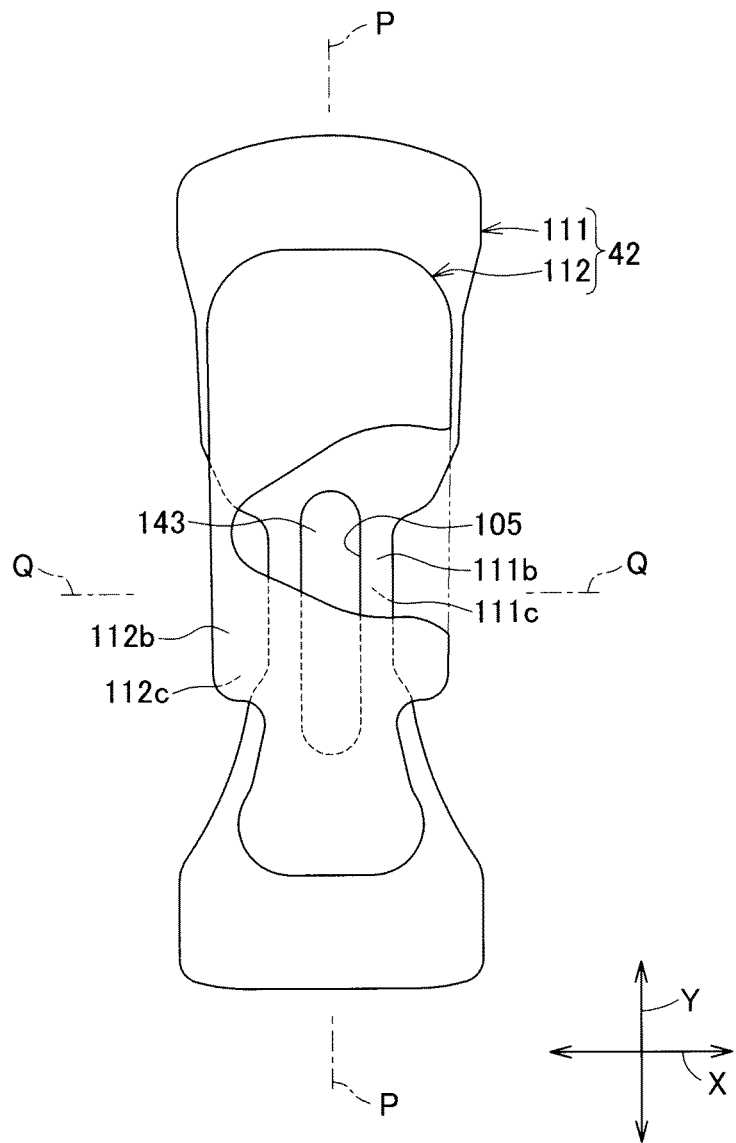
FIG. 11 is a plan view of a core according to one exemplary embodiment of the present invention.

Referring to FIG. 11, the core 42 includes a first core layer 111 lying on the non-skin-facing surface of the panel 40 and a second core layer 112 lying on the skin-facing surface of the panel 40. The first core layer 111 contains fluff wood pulp fibers 101 at a rate ranging from about 100 to about 500 g/m$^2$ and superabsorbent polymer particles at a rate ranging from about 20 to about 500 g/m$^2$. The first core layer 111 has a planar shape slightly differing from a planar shape of the core 42 in FIG. 7 and is formed along the longitudinal center line P-P with an elongated depression 143 in the form of a through-hole. The second core layer 112 contains fluff wood pulp fibers 101 at a rate ranging from about 100 to about 500 g/m$^2$ and superabsorbent polymer particles 102 at a rate ranging from 0 to about 500 g/m$^2$. A length dimension of the second core layer 112 in the longitudinal direction Y is shorter than the corresponding dimension of the first core layer 111. In the crotch region 14 (See FIG. 2), a width dimension of the second core layer 112 is larger than the corresponding width dimension of the first core layer 111. The first core layer 111 is formed along the longitudinal center line P-P with the elongated depression 143 sinking between a top surface 111b put in contact with the second core layer 112 and a bottom surface 111c put in contact with the backsheet 22. The elongated depression 143 may, however, be provided in the form of grooves each having a relatively thin bottom. The second core layer 112 has a top surface 112b and a bottom surface 112c both formed with no elongated depression. The first core layer 111 is additionally formed on the bottom surface 111c and a peripheral wall 143a of the elongated depression 143 with surface layers 104a, 105a, respectively, leaving the remainder to define inner section 106a. The second core layer 112 is formed only on the bottom surface 112c with a surface layer 104b. These surface layers 104a, 105a are formed only or mostly of fluff wood pulp fibers used as the liquid-absorbent fibers like the surface layers 104, 105 in FIG. 6. These surface layers serve as the barriers against the superabsorbent polymer particles 102 which might otherwise intrude from the inner section 106a into the elongated depression 143. The surface layer 104b of the second core layer 112 serves as a barrier against the superabsorbent polymer particles 102 which might otherwise move from the second core layer 112 toward the first core layer 111. In the core 42 shown in FIG. 11, the elongated depression 143 serving to assist dispersion of bodily fluids is provided in the form of the elongated depression 143 in the first core layer 111 and, as viewed in a thickness direction, the upper opening of the elongated depression 143 is closed by the surface layer 104b of the second core layer 112.

Figure 12:
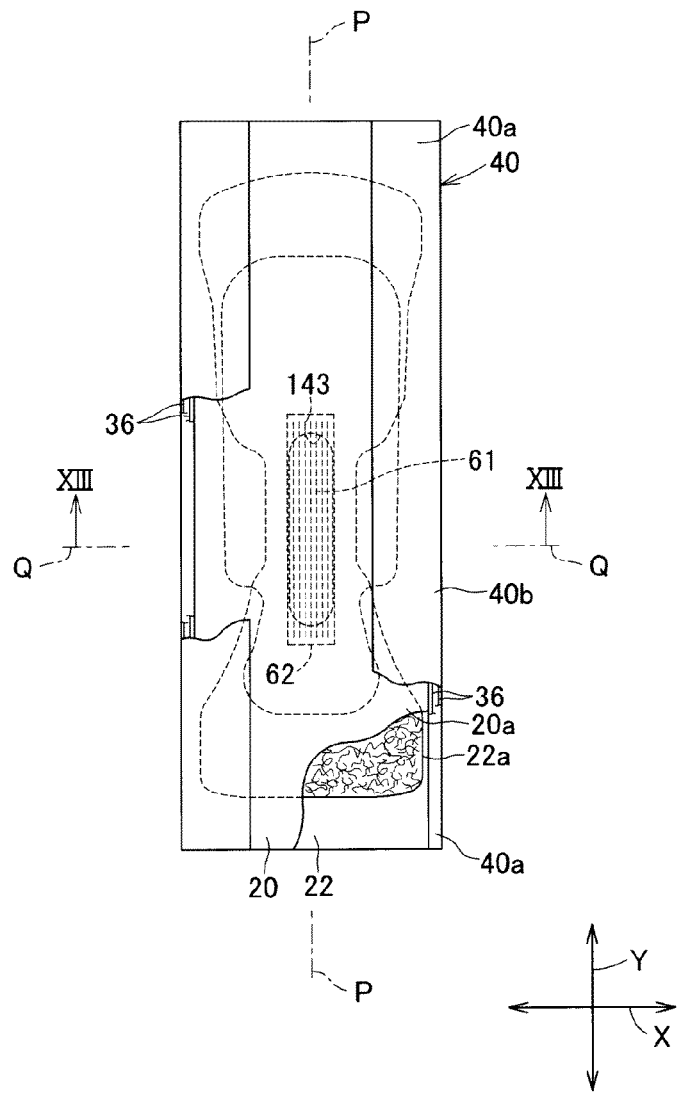
FIG. 12 is a plan view exemplarily illustrating a manner in which the core of FIG. 11 is actually used.
Figure 13:
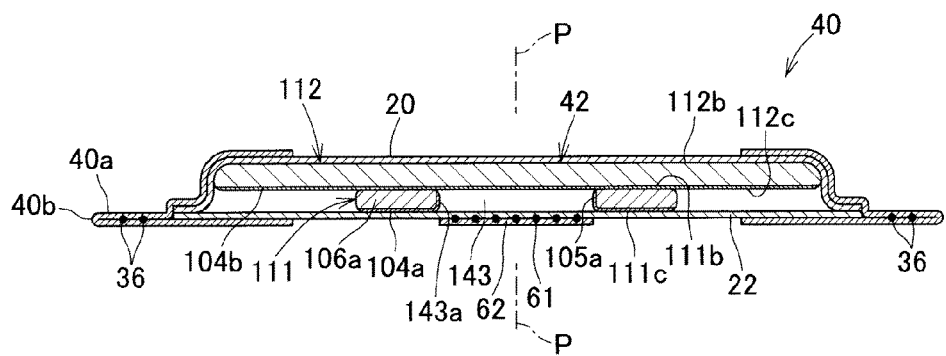
FIG. 13 is a sectional view of the core taken along line XIII-XIII in FIG. 12.

In the panel 40 of FIGS. 12 and 13 including the core 42 of FIG. 11, the backsheet 22 is provided on its outer surface with a plurality of central elastic members 61 extending across the elongated depression 143 in the longitudinal direction. Specifically, these central elastic members 61 are disposed between the backsheet 22 and an elastic member covering sheet 62 and secured under tension in the longitudinal direction Y to at least one of these sheets 22, 62 with hot melt adhesives (not shown). The elastic member covering sheet 62 may be formed of nonwoven fabrics or plastic films.

Figure 14:
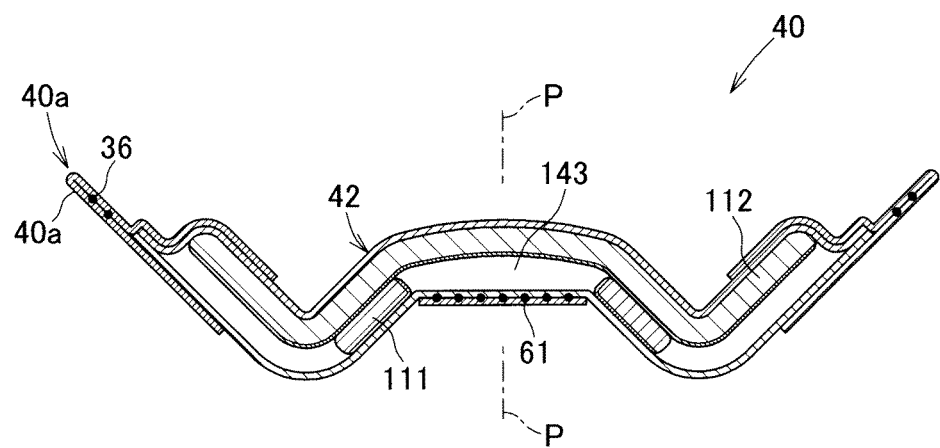
FIG. 14 is a diagram exemplarily illustrating a manner in which the core of FIG. 13 is deformed.

FIG. 14 is a view similar to FIG. 13, exemplarily showing a manner in which the panel 40 of FIG. 13 is deformed. With the diaper 10 on the wearer's body, assuming that not the panel shown in FIG. 2 but the panel 40 shown in FIGS. 12 and 13 is attached to the chassis 11, the elastic members 61 will be elastically stretched in the longitudinal direction Y to bring a region of the panel defined along the elastic members 61 closer to or in contact with the wearer's crotch region. In addition, the elastic members for the gasket cuffs 40*a* are also stretched in the longitudinal direction Y or in the circumferential direction around the wearer's legs to bring the side edges 40*b* of the respective gasket cuffs 40*a* closer to or in contact with the wearer's legs or inguinal regions. In such situation, a cross-sectional shape of the panel 40 taken along the transverse center line Q-Q is deformed nearly to a W-shape as exemplarily shown in FIG. 14 wherein the elastic members 61 and the elastic members 36 generate crests and an intermediate segment extending between the elastic members 61, 36 define troughs. Such diaper 10 uniquely designed so that the panel 40 is deformed in this manner under the effect of the elastic members 61 and thereby the panel 40 is brought close to or in contact with the wearer's crotch region is particularly suitable for the patient suffering from mid or moderate degree of incontinence. In other words, such diaper 10 has a beneficial effect on absorption of a relatively small quantity of urine discharged usually at a slow rate. The elongated depression 143 formed in the first core layer 111 is the basic feature of the functions to assist dispersion of bodily fluids in a manner similar to that described with respect to the elongated depression 43 exemplarily shown in FIGS. 4 through 6 and, in addition, cooperates with the elastic members 61 to facilitate the core 42 to be deformed about the longitudinal center line P-P in an inverted V-shape and thereby to facilitate the panel 40 as a whole to be deformed into a W-shape. With the unique dimensioning in the crotch region 14 of the core 42 such that the width dimension of the first core layer 111 is smaller than the width dimension of the second core layer 112 so as to define a step in the thickness of the core 42, the core 42 can be easily bent along this step and thereby easily deformed into a W-shape. It should be appreciated here that the core 42 shown in FIG. 11 may be implemented without being combined with the elastic members 61, i.e., by the core 42 alone.

Figure 15:
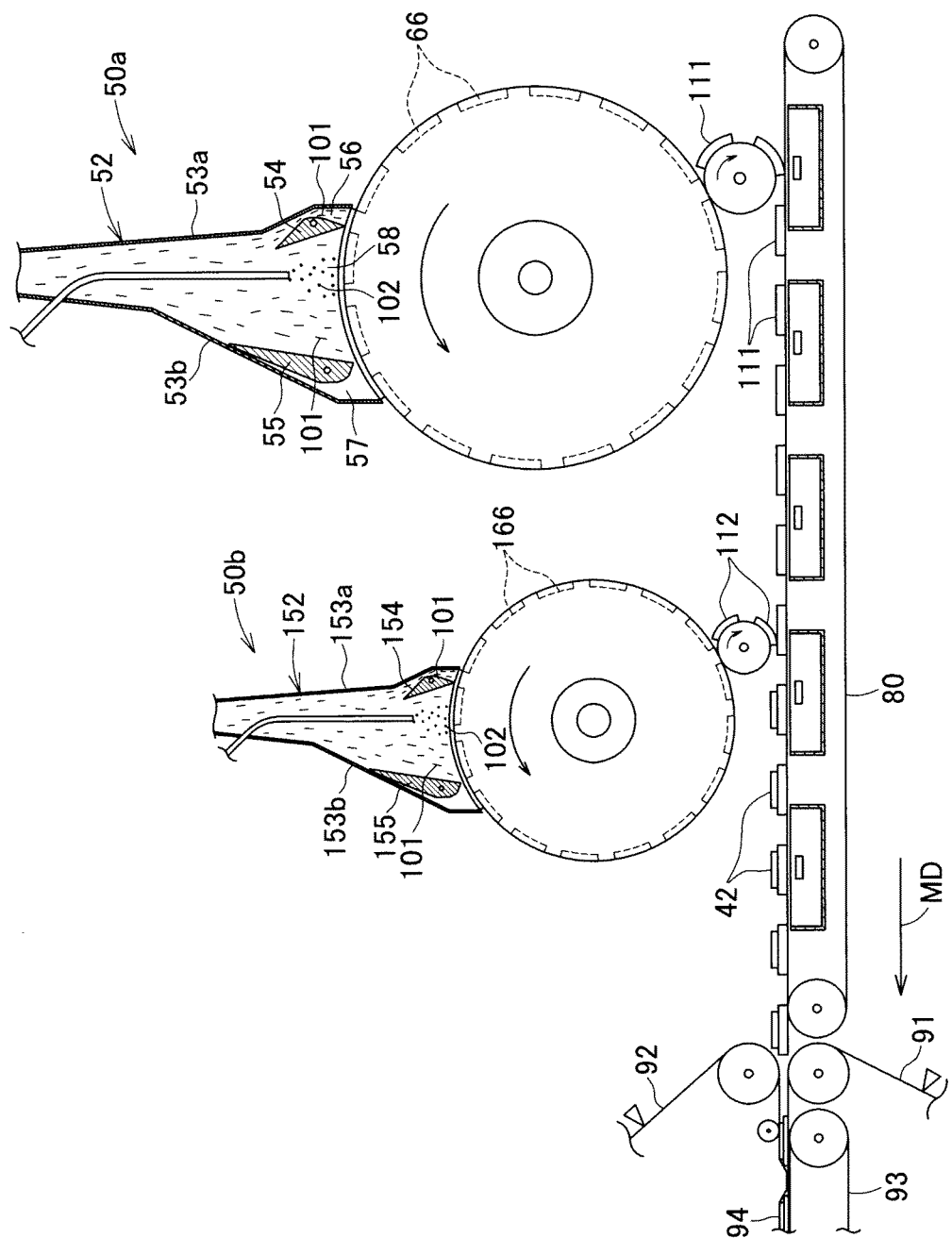
FIG. 15 is a diagram illustrating a process for making the core of FIG. 11.

FIG. 15 is a diagram similar to FIG. 8, illustrating a part of a process for making the core 42 of FIG. 11 wherein first and second apparatuses 50*a*, 50*b* are illustrated as being partially cutaway. The process illustrated in FIG. 15 involves, in addition to the first and second apparatuses 50*a*, 50*b*, the first and second conveyor belts 80, 93 and the supplying means for a first web 91 and a second web 92. The first and second apparatuses 50*a*, 50*b*, the first and second conveyor belts 80, 93 and the supplying means for a first web 91 and a second web 92 are generally similar to the apparatus 50, the first and second conveyor belts 80, 93 and the supplying means for first web 91 and second web 92, respectively, in FIGS. 8 and 9. The second apparatus 50*b* corresponds to a downsized version of the first apparatus 50*a* and has substantially the same construction thereof is substantially the same as the first apparatus 50*a* except that, in the process of FIG. 15, the first core layer 111 of the core 42 is formed by the first apparatus 50*a* and the second core layer 112 is formed by the second apparatus 50*b*. To make it possible, the first apparatus 50*a* includes the molds 66 each having a configuration corresponding to the one of the first core layer 111 with elongated depressions 143 described later and the second apparatus 50*b* includes molds 166 each having a configuration corresponding to the one of the second core layer 112 with elongated depressions 243 described later. In the conduit 52 of the first apparatus 50*a*, the first movable partition wall 54 is kept to be spaced from the peripheral wall 53*a* of the conduit 52 and thereby the first divergent pathway is kept open while the second movable partition wall 55 is kept in contact with the peripheral wall 53*b* of the conduit 52 and thereby the second divergent pathway is kept closed in order that the first core layer 111 can be formed with the surface layers 104*a*, 105*a* (See FIG. 13). In the second apparatus 52*b*, a first movable partition wall 154 is kept to be spaced from a peripheral wall 153*a* of a conduit 152 while a second movable partition wall 155 is kept in contact with a peripheral wall 153*b* of the conduit 152 in order that the second core layer 112 can be formed with the surface layer 104*b*. The first core layer 111 formed by the first apparatus 50*a* and the second core layer 112 formed by the second apparatus 50*b* are stacked one on another to form the core 42. The core 42 is further worked on to form the composite web which is conveyed to the downstream side in the machine direction MD. In the steps on the downstream side, the web of gasket cuffs 40*a*, the elastic members 61 and the elastic member covering sheet 62 are attached to the composite web. These steps are not shown for convenience of illustration. While the process of FIG. 15 also may include the step of press-working the core 42 at an appropriate stage of the process, this step is not shown for convenience of illustration.

Figure 16:
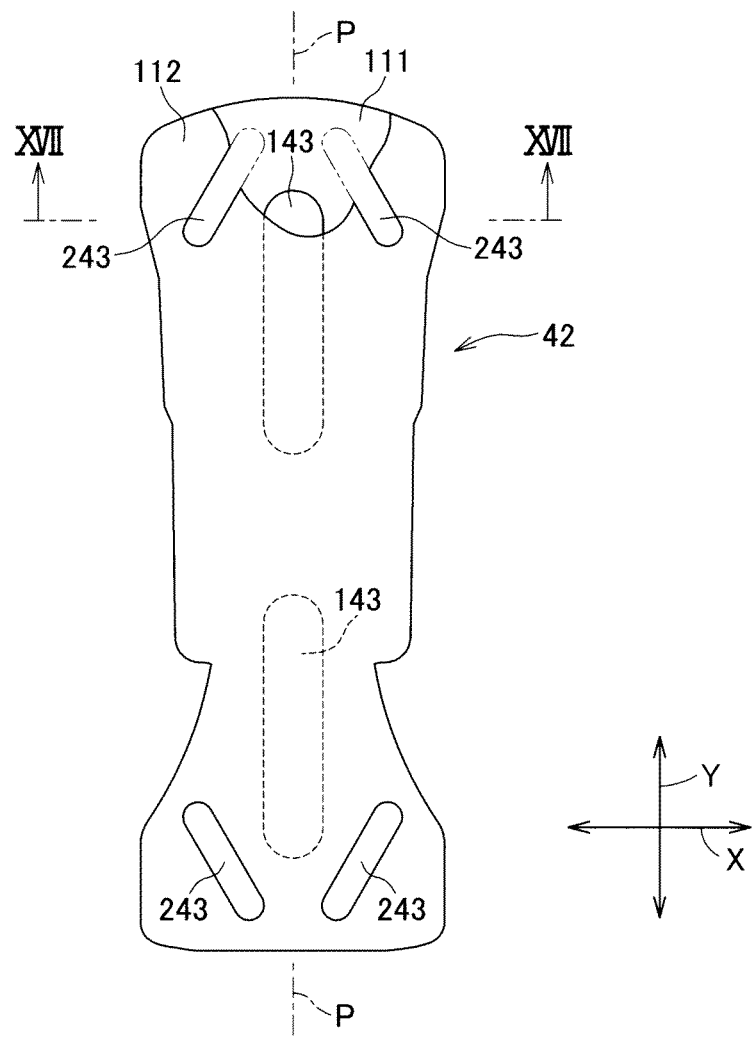
FIG. 16 is a plan view similar to FIG. 11, showing a core in accordance with another embodiment of the present invention.
Figure 17:
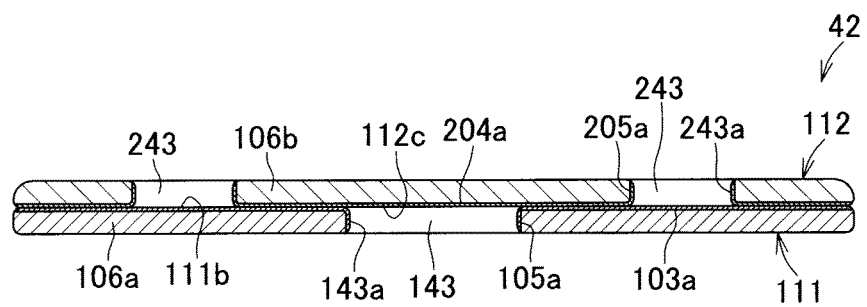
FIG. 17 is a sectional view of the core taken along line XVII-XVII in FIG. 16.

FIG. 16 is a view similar to FIG. 7, exemplarily showing another embodiment of the core 42 and FIG. 17 is a sectional view taken along line XVII-XVII in FIG. 16. The core 42 of FIG. 16 includes the first core layer 111 and the second core layer 112 stacked one on another. While the first and second core layers 111, 112 are not different from each other so far as the shape and the size are concerned, the first core layer 11 defining the lower layer in the core 42 is formed along the longitudinal center line P-P with a pair of elongated depressions 143 spaced from each other in the longitudinal direction Y. The second core layer 112 defining the upper layer in the core 42 is formed in vicinities of four corners with elongated depressions 243, respectively. In the first core layer 111, the top surface 111*b* and the respective peripheral walls 143*a* of the elongated depressions 143 are respectively formed with the surface layers 103*a*, 105*a* made mostly of liquid-absorbent fibers (not shown) accumulated thereon. In the second core layer 112, the bottom surface 112*c* and peripheral walls of the respective elongated depressions 243 are formed with surface layers 204*a*, 205*a* made mostly of liquid-absorbent fibers (not shown) accumulated thereon. The elongated depression 143 of this core 42 are according to one of variants of the elongated depressions to be formed in the core 42 and advantageously function to facilitate bodily fluids flowing thereinto to flow and to disperse in the longitudinal direction Y and simultaneously function to facilitate the peripheral walls 143*a* to absorb bodily fluids. In addition, the elongated depressions 143 function as barriers adapted to prevent the superabsorbent polymer particles (not shown) contained in the inner sections 106*a*, 106*b* from intruding into the elongated depressions 143, 243. Furthermore, these elongated depressions 143 facilitate the panel 40 to be bent along the longitudinal center line P-P in an inverted V-shape with the second core layer 112 facing outward and thereby facilitate the region of the panel 40 along the longitudinal center line P-P to be brought closer to or in contact with the diaper wearer's crotch region. The elongated depressions 243 with elongated depressions of the core 42 formed in the core 42 and function not only to facilitate absorption and dispersion of bodily fluids but also to facilitate the corners of the panel 40 to be deformed. The elongated depressions 243 may, however, be provided in the form of grooves each having a relatively thin bottom. In consequence, these corners should not uncomfortably compress the wearer's skin.

Figure 18:
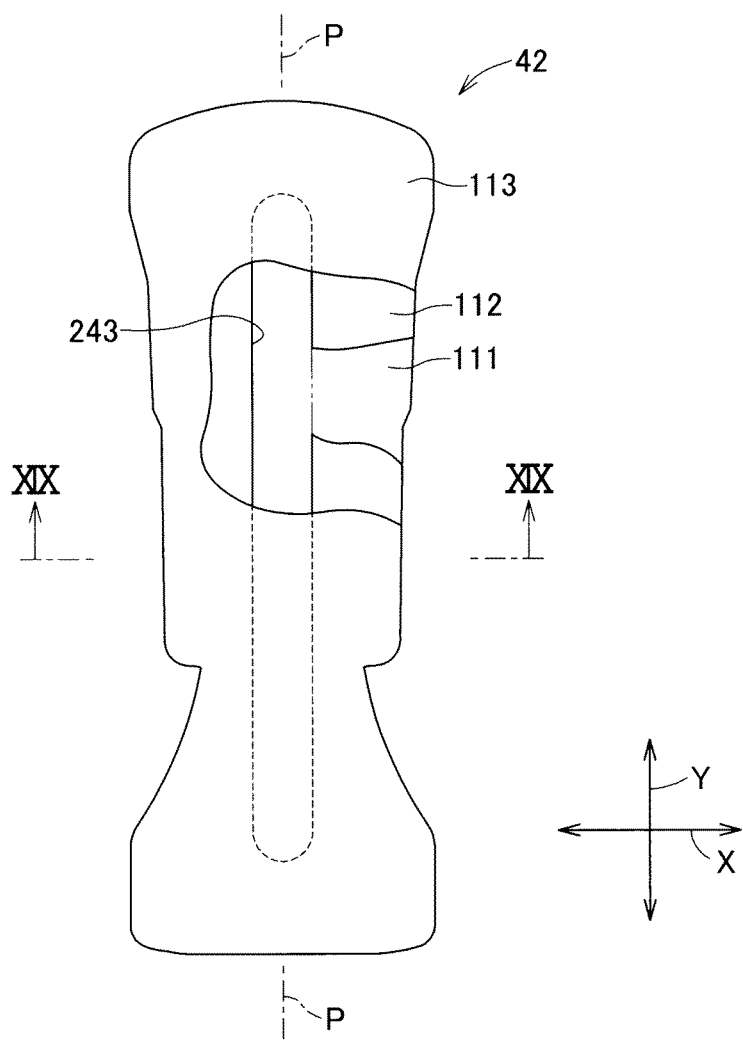
FIG. 18 is a plan view of the core similar to FIG. 11, showing still another embodiment of the core.
Figure 19:
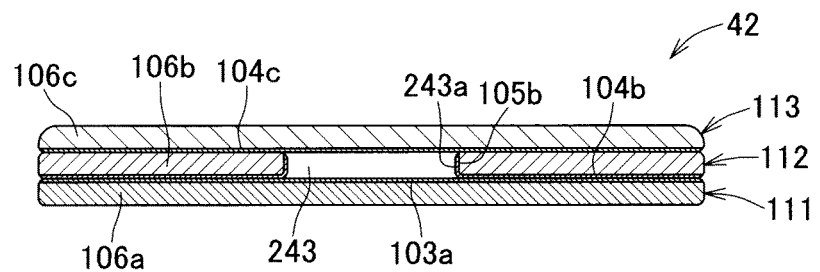
FIG. 19 is a sectional view of the core taken along line XIX-XIX in FIG. 18.

FIG. 18 is a view similar to FIG. 7, exemplarily showing still another embodiment of the core 42 and FIG. 19 is a sectional view taken along Line XIX-XIX in FIG. 18. The core 42 shown in FIGS. 18 and 19 includes first, second and third core layers 111, 112, 113 which are uniform in shape as well as in size and stacked one on another. The second core layer 112 is sandwiched between the first and second core layers 111, 113 and formed along the longitudinal center line P-P with an elongated depression 243 which is relatively long in the longitudinal direction Y. The first core layer 111 is formed on its top surface with the surface layer 103a including primarily liquid-absorbent fibers (not shown) accumulated thereon. The second core layer 112 is formed on its bottom surface and a peripheral wall 243a of the elongated depression 243 with the surface layers 104b, 105b including primarily liquid-absorbent fibers (not shown) accumulated thereon. The third core layer 113 is formed on its bottom surface with the surface layer 104c including primarily liquid-absorbent fibers (not shown) accumulated thereon. These surface layers 103a, 104b, 105b, 104c also advantageously function not only to prevent superabsorbent polymer particles (not shown) contained in the respective inner sections 106a, 106b, 106c from intruding into the elongated depression 243 but also to assist dispersion and absorption of bodily fluids in the elongated depression 243. The elongated depression 243 facilitates the panel 40 to be deformed along the longitudinal center line P-P into the inverted V-shape.

Such core 42 may include the first and second core layers 111, 112, the second core layer 112 may be formed with the elongated depression 243 in the form of through-hole and the third core layer 113 may be stacked on the second core layer 112 so that an upper opening of the elongated depression formed in the upper surface of the second core layer 112 may be closed by fluff wood pulp fibers forming the third core layer 113.

The core 42 according to the invention exemplarily illustrated in FIGS. 11 through 18 also may be used as the bodily fluid absorbent core in various bodily fluid absorbent articles, such as incontinent briefs and menstruation pads by making appropriate changes to its shape, thickness or configuration of the elongated depression 43 or 243.

The first aspect of the invention described above may be arranged in at least the following items:

(i) A bodily fluid absorbent article, including:
a bodily fluid absorbent core having a predetermined thickness and containing therein liquid-absorbent fibers and superabsorbent polymer particles; and
a liquid-pervious sheet covering an upper surface of the core.

In the bodily fluid absorbent article, the core has a skin-facing surface and a non-skin-facing surface opposite to the skin-facing surface;
at least one of the skin-facing surface and the non-skin-facing surface is formed with one or more elongated depressions sinking from the skin-facing surface toward the non-skin-facing surface; and
the core includes one or more surface layers each formed of the liquid-absorbent fibers to define a peripheral wall or peripheral walls of the one or more elongated depressions, and an inner section lying inside the one or more surface layers and formed of the liquid-absorbent fibers and the superabsorbent polymer particles mixed together.

The first aspect may include one or more of the following embodiments.

(ii) The one or more elongated depressions are provided in the form of through-holes extending from the skin-facing surface to the non-skin-facing surface.

(iii) The one or more elongated depressions are provided in the form of grooves each having a bottom.

(iv) The core has a longitudinal direction and a transverse direction being orthogonal to each other;
the core is formed in the middle thereof as viewed in the transverse direction with the one or more elongated depressions;
the non-skin-facing surface of the core is covered with a liquid-impervious sheet; and
the liquid-impervious sheet is provided with elastic members extending in parallel to the one or more elongated depressions secured under tension thereto.

(v) The core includes a plurality of core layers stacked one on another;
any one of these core layers is formed with the one or more elongated depressions; at least one of the elongated depressions have respective openings in a thickness direction of the core; and
the openings are closed by the liquid-absorbent fibers contained in the core layer stacked directly on the core layer formed with the one or more elongated depressions.

(vi) Each of the core layers has surface layers and medial regions surrounded by the surface layers wherein the surface layers contain the fluff wood pulp fibers at higher ratio comparing to the superabsorbent polymer particles than the medial regions.

The second aspect of the invention may be arranged in at least the following items:

(vii) A method for making a bodily fluid absorbent core in a bodily fluid absorbent article, wherein
a process for making the core includes a step of feeding liquid-absorbent fibers to respective molds each having a concave area corresponding to a three-dimensional shape of the core wherein the concave area is defined by a bottom and a peripheral wall rising from the bottom;
the respective peripheral walls of the molds are at least partially formed with a plurality of through-holes via which the one or more concave areas is capable of being subjected to a suction effect; and
in the fiber feeding step, respective surfaces of the peripheral walls are at least partially covered with the liquid-absorbent fibers under the suction effect provided via the through-holes.

The second aspect of the invention may include at least the following embodiments:

(viii) The respective bottoms of the molds also are formed with a plurality of through-holes via which the suction effect is capable of being provided; and
the process includes a first step of at least partially covering the bottoms and the peripheral walls of the respective molds with the liquid-absorbent fibers under the suction effect provided via the through-holes and a second step of feeding the liquid-absorbent fibers and the superabsorbent polymer particles to the respective concave areas of the molds after the first step.

One or more aspects of the invention described in the above items (i) through (viii) may provide one or more of the following advantageous effects.

The surface layers defining the peripheral walls of the one or more elongated depressions of the bodily fluid absorbent core for the article are primarily formed of the liquid-absorbent fibers. With such unique feature, it is possible for these surface layers to prevent the super liquid-absorbent polymer particles contained in the inner sections from moving in the core and intrude into the elongated depressions where the super absorbent polymer particles may absorb bodily fluids and form a gel block inside the one or more elongated depressions. In this way, it is possible for this bodily fluid absorbent core to absorb bodily fluids through the peripheral walls of the one or more elongated depressions.

This application claims the benefit of Japanese Application No. 2010-294192 the entire disclosure of which is incorporated by reference herein. Although the invention has been described in its preferred form with a certain degree of particularity, it is understood that the present disclosure of the preferred form has been changed in the details of construction and the combination and arrangement of parts may be resorted to without departing from the and the spirit and the scope of the invention as hereinafter claimed.

The invention claimed is:

1. A bodily fluid absorbent article, comprising:
   a bodily fluid absorbent core having a predetermined thickness and including therein liquid-absorbent fibers and superabsorbent polymer particles;
   a liquid-pervious sheet covering a skin-facing surface of the core;
   a liquid-impervious sheet covering a non-skin-facing surface of the core; and
   elastic members secured under tension to the liquid-impervious sheet,
   wherein
   the non-skin-facing surface is opposite to the skin-facing surface,
   the core has one or more elongated depressions sinking from the skin-facing surface toward the non-skin-facing surface,
   the core comprises
      one or more surface layers each formed of the liquid-absorbent fibers to define a peripheral wall or peripheral walls of the one or more elongated depressions, and
      an inner section covered by the one or more surface layers and formed of the liquid-absorbent fibers and the superabsorbent polymer particles mixed together,
   said one or more elongated depressions are through-holes extending from the skin-facing surface to the non-skin-facing surface,
   the core has a longitudinal direction and a transverse direction being orthogonal to each other,
   the core includes the one or more elongated depressions in a middle of the core as viewed in the transverse direction, and
   the elastic members extend across the one or more elongated depressions in the longitudinal direction.

2. The bodily fluid absorbent article defined by claim 1, wherein
   the core comprises a plurality of core layers stacked one on another;
   any one of the plurality of core layers is formed with the one or more elongated depressions;
   at least one of the elongated depressions have respective openings in a thickness direction of the core; and
   the openings are closed by the liquid-absorbent fibers contained in the core layer stacked directly on the core layer formed with the one or more elongated depressions.

3. The bodily fluid absorbent article defined by claim 2, wherein
   each of the core layers has surface layers and inner regions surrounded by the surface layers, and
   the surface layers contain fluff wood pulp fibers at a higher ratio than a ratio of the superabsorbent polymer particles in the inner regions.

4. The bodily fluid absorbent article defined by claim 1, wherein the elastic members secured to the liquid-impervious sheet are located on a non-skin facing side of the liquid-impervious sheet.

5. The bodily fluid absorbent article defined by claim 1, wherein
   the one or more elongated depressions have a greater length in the longitudinal direction than in the transverse direction, and
   a length of the elastic members in the longitudinal direction is greater than the length of the one or more elongated depressions in the longitudinal direction.

6. The bodily fluid absorbent article defined by claim 1, further comprising an elastic member covering sheet,
   wherein the elastic members are sandwiched between the liquid-impervious sheet and the elastic covering sheet.

7. The bodily fluid absorbent article defined by claim 6, wherein a width of the elastic covering sheet in the transverse direction is same as a width of the one or more elongated depressions in the transverse direction.

* * * * *